(12) United States Patent
Munoz et al.

(10) Patent No.: US 8,021,311 B2
(45) Date of Patent: Sep. 20, 2011

(54) MECHANICAL HONING OF METALLIC TUBING FOR SOLDERING IN A MEDICAL DEVICE CONSTRUCTION

(75) Inventors: Michael Munoz, Waverly, MN (US);
Scott Solberg, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 536 days.

(21) Appl. No.: 11/504,852

(22) Filed: Aug. 16, 2006

(65) Prior Publication Data
US 2008/0097248 A1    Apr. 24, 2008

(51) Int. Cl.
*A61B 5/00* (2006.01)
(52) U.S. Cl. .......................................... 600/585
(58) Field of Classification Search .................... 600/585
See application file for complete search history.

(56) References Cited

U.S. PATENT DOCUMENTS

| | | | |
|---|---|---|---|
| 4,024,303 A | 5/1977 | Hahn | |
| 5,009,966 A | 4/1991 | Garg et al. | |
| 5,106,455 A | 4/1992 | Jacobsen et al. | |
| 5,242,759 A | 9/1993 | Hall | |
| 5,354,623 A | 10/1994 | Hall | |
| 6,419,693 B1 | 7/2002 | Fariabi | |
| 6,659,329 B1 | 12/2003 | Hall | |
| 6,669,534 B2 * | 12/2003 | Shirzadi Ghoshouni et al. | 451/28 |
| 6,766,720 B1 | 7/2004 | Jacobsen et al. | |
| 2002/0130007 A1* | 9/2002 | Nakamura et al. | 192/38 |
| 2003/0069522 A1 | 4/2003 | Jacobsen et al. | |
| 2004/0181174 A2* | 9/2004 | Davis et al. | 600/585 |
| 2005/0072837 A1 | 4/2005 | Nanis | |
| 2005/0124917 A1* | 6/2005 | Skujins et al. | 600/585 |
| 2005/0145307 A1* | 7/2005 | Shireman et al. | 148/565 |
| 2005/0175421 A1* | 8/2005 | Hall | 407/33 |
| 2007/0042325 A1* | 2/2007 | Florman | 433/116 |
| 2007/0240906 A1* | 10/2007 | Hill | 175/57 |
| 2008/0156480 A1* | 7/2008 | Cook et al. | 166/212 |

FOREIGN PATENT DOCUMENTS

| | | |
|---|---|---|
| EP | 0 515078 * | 5/1992 |
| EP | 0 515 078 A2 | 11/1992 |
| EP | 1 419 797 A1 | 5/2004 |
| WO | 0040286 A1 | 7/2000 |
| WO | 03047677 A1 | 6/2003 |
| WO | 2005087303 A1 | 9/2005 |

OTHER PUBLICATIONS

Slemp et al. "Microblasting: Expanding Options" MDDI Apr. 2003 pp. 1-7.*

* cited by examiner

*Primary Examiner* — Max Hindenburg
*Assistant Examiner* — Renee Danega
(74) *Attorney, Agent, or Firm* — Seager, Tufte & Wickhem, LLC (57) ABSTRACT

Medical devices and methods for manufacturing medical devices. An example manufacturing method includes providing a metallic tubular member having a inner surface with a metal oxide layer disposed thereon, mechanically scoring and/or removing a portion of the metal oxide layer to create a bonding zone along the inner surface, and soldering an additional metallic structural element to the bonding zone.

34 Claims, 7 Drawing Sheets

MECHANICAL HONING OF METALLIC TUBING FOR SOLDERING IN A MEDICAL DEVICE CONSTRUCTION

FIELD OF THE INVENTION

The present invention pertains to medical devices, and methods for manufacturing medical devices. More particularly, the present invention pertains to elongated intracorporeal medical devices including an elongated metallic tubular member connected with other structures, and methods for manufacturing such devices.

BACKGROUND

A wide variety of intracorporeal medical devices have been developed for medical use, for example, intravascular use. Some of these devices include guidewires, catheters, stents, and the like. These devices are manufactured by any one of a variety of different manufacturing methods. Of the known medical devices and manufacturing methods, each has certain advantages and disadvantages. There is an ongoing need to provide alternative medical devices as well as alternative methods for manufacturing medical devices.

BRIEF SUMMARY

The invention provides design, material, and manufacturing method alternatives for medical devices. An example embodiment relates to a method for manufacturing a medical device. An elongate metallic tubular member is provided defining an inner lumen and having an inner surface, the inner surface including a metal oxide formed thereon. At least a portion of the inner surface is mechanically scored to remove at least some of the metal oxide to create a bonding zone along the inner surface, and an additional structural element is soldered to the bonding zone. Other example embodiments relate to an elongated medical device including an elongate metallic tubular member defining an inner lumen and having an inner surface. A portion of the inner surface of the metallic tubular member is mechanically scored to define a bonding zone having a reduced amount of metal oxide. An additional structural element is soldered to the inner surface at the bonding zone. In some embodiments, the metallic tubular member can include a nickel-titanium alloy.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
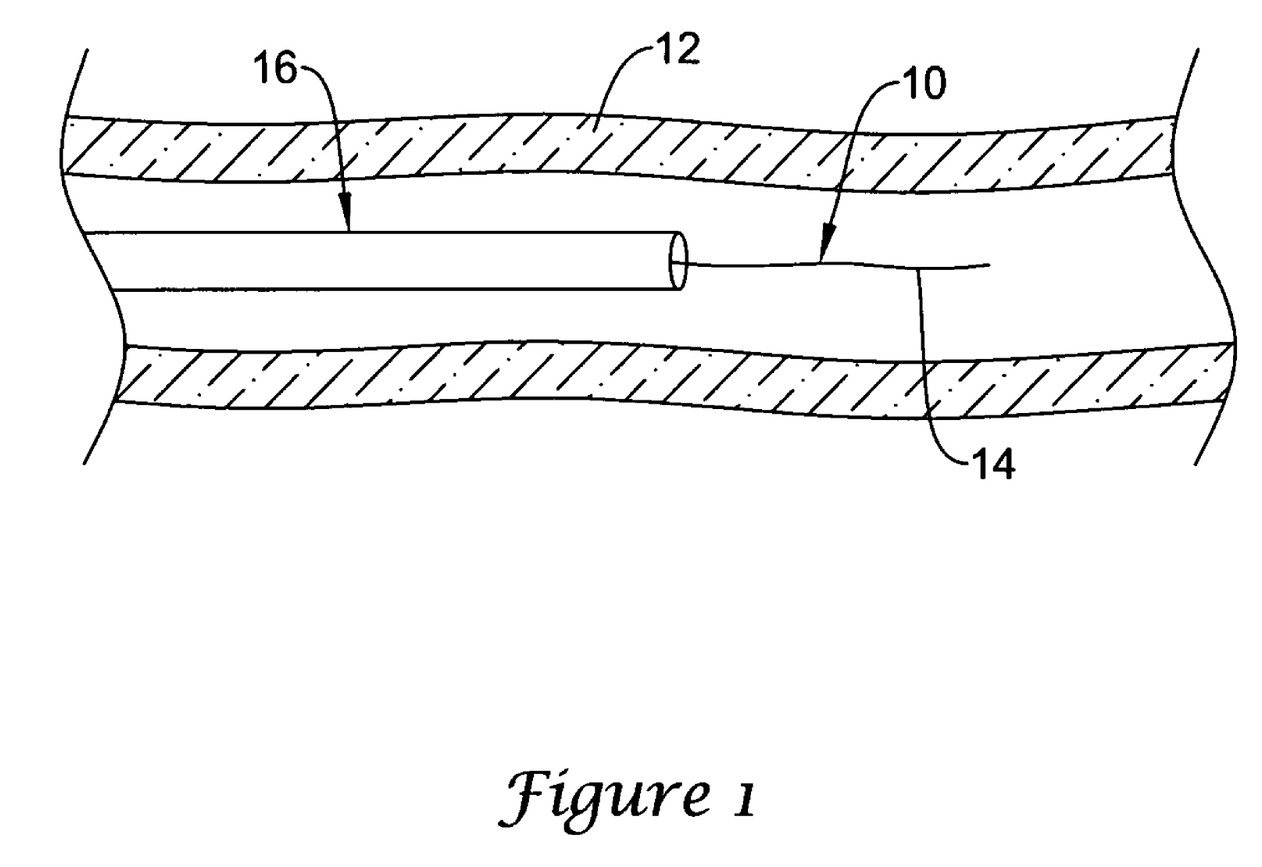
FIG. 1 is a plan view of an example medical device disposed in a blood vessel.

FIG. 1 is a plan view of an example guidewire 10 disposed in a blood vessel 12. Guidewire 10 may include a distal section 14 that may be, as is well known in the art, generally configured for probing within the anatomy of a patient. Guidewire 10 may be used for intravascular procedures according to common practice and procedure. For example, guidewire 10 may be used in conjunction with another medical device such as a catheter 16. Of course, numerous other uses are known amongst clinicians for guidewires and other similarly configured medical devices.

Figure 2:
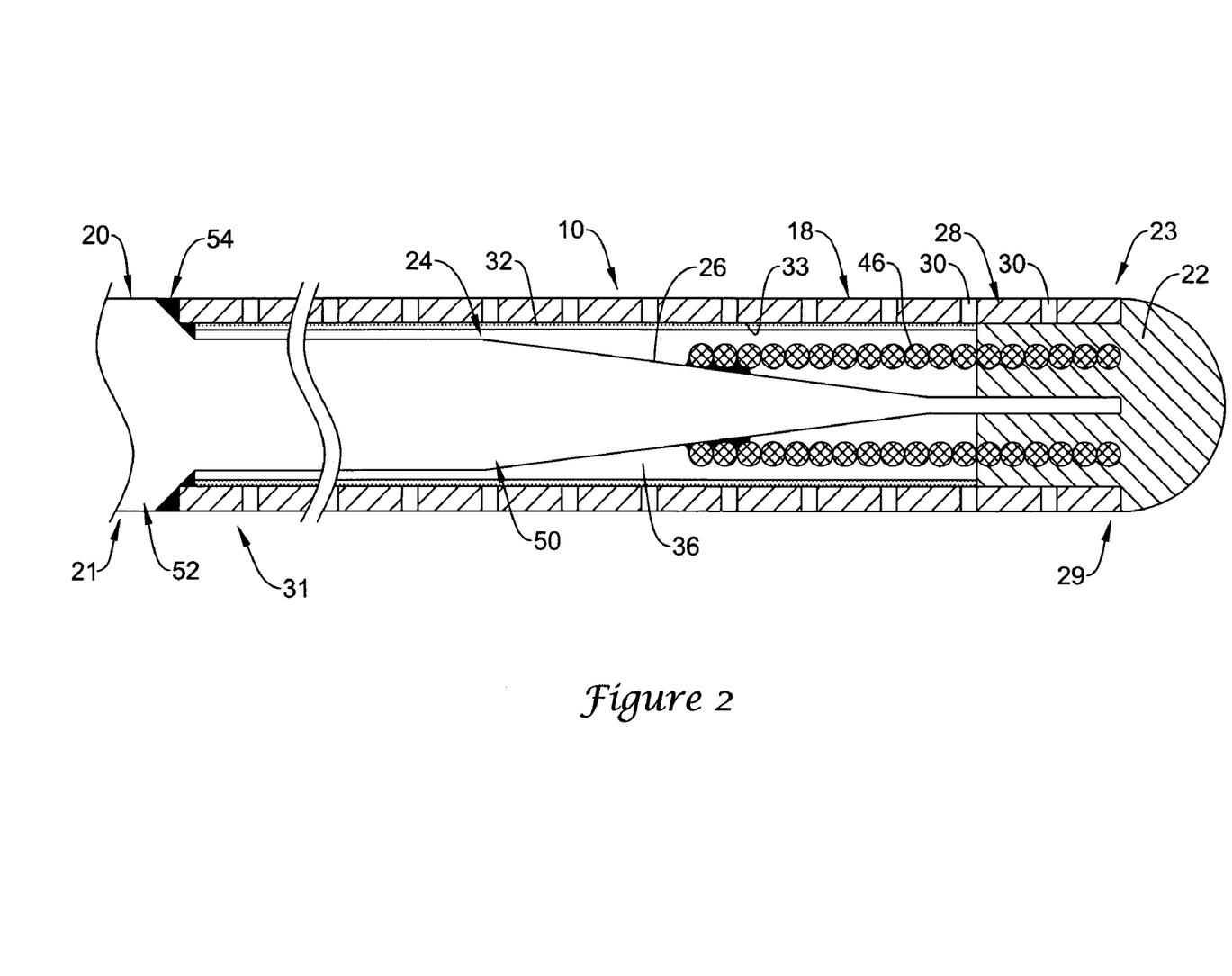
FIG. 2 is a partial cross-sectional side view of an example medical device.

Turning now to FIG. 2, here some of the various components of an example guidewire 10 are shown. Guidewire 10 can include a distal region 18, a proximal region 20, and a proximal end 21 and a distal end 23. As used herein, the distal region 18 and the proximal region 20 may generically refer to any two adjacent guidewire sections along any portion of the guidewire 10. In some embodiments, the distal region 18 may be generally more laterally flexible, and the proximal region 20 may be generally more laterally stiff. The guidewire 10 includes a generally tubular metallic member 28 that includes a distal end 29 and a proximal end 31, and defines an inner lumen 36 having an inner surface 33. The tubular member 28 may extend longitudinally along a longitudinal axis. In some embodiments, the tubular member 28 may include a plurality of slots or cuts 30 formed in at least a portion thereof. Some additional aspects of the tubular member 28 will be discussed in more detail below.

A distal tip member 22 may be disposed at the distal end 29 of the tubular member 28 and/or the distal end 23 of the guidewire 10, and may be attached, for example, to a portion of the inner surface 33 of the tubular member 28. The distal tip member 22 may be any or a broad variety of suitable structures, for example, a solder tip, a pre-made or pre-formed metallic structure, or the like, that is attached or joined to the distal end of the tubular member 28 using a suitable attachment technique, some of which will be discussed further below.

The guidewire 10 may also include a core member 24 that may be attached to the metallic tubular member 28, and extend from a location within the tubular member 28 and/or from the proximal end 31 of the tubular member 28 to the proximal end of the guidewire 10. As can be appreciated, a portion of the core member 24 may extend into at least a portion of the lumen 36. In the embodiment shown, the core member 24 includes a distal portion 50 that extends within the lumen 36, and a proximal portion 52 that extends proximally from the tubular member 28. The core member 24 can be attached to the tubular member 28 in any suitable manner and at any suitable location. For example, the core member 24 may be attached to the tubular member 28 through one or more attachment areas 54, which in this embodiment are disposed adjacent the proximal end 31 of the tubular member 28. It should be understood that additional attachment areas, and/or alternative positioning of attachment areas may be used in other embodiments. The core member 24 may also extend to, and be attached to the distal tip member 22, for example, as discussed in more detail below. In other embodiments, however, the core member 24 may end proximally from the distal tip member 22 and/or proximally of the distal end 29 of the tubular member 28. In some such embodiments, a shaping structure, such as a shaping ribbon, wire, or coil, may be attached to and extend distally from the distal end of the core member 24, and be attached to the distal tip 22.

Additionally, in other embodiments, the core member 24 may be absent, and/or the tubular member 28 may extend to the proximal end of the guidewire 10. For example, in some other embodiments, the tubular member 28 may extend along substantially the entire length of the guidewire 10, for example, form the proximal end 21 to the distal end 23 of the guidewire 10, and the core member 24 may be present and disposed within at least a portion of the tubular member 28, or may be absent, as desired. In addition, it should be understood that other structure or components, may be used in the guidewire construction, such as a shaping wire or ribbon, one or more coils, marker members, or the like, or others, some of which are discussed below. For example, in the embodiment shown, a coil 46 is disposed within the tubular member 28 and/or about a portion of the core wire 24.

As can be appreciated, it may be desirable to make attachments between the inner surface 33 of the metallic tubular member 28 and other components of the guidewire, for example, using soldering techniques, or the like. For example, it may be desirable to solder one or more of the distal tip member 22, the core wire 24, the coil and/or other structure that may be present within the guidewire 10 to the inner surface 33 of the metallic tubular member 28. However, metal parts and/or components often utilized when manufacturing medical devices including, for example, the metallic tubular member 28, can include surfaces that have become oxidized (i.e., have a metal oxide layer formed thereon), for example, through exposure to the environment. For example, referring to FIG. 2, the metallic tubular member 28 may have a metal oxide layer 32 formed along an inner surface 33 thereof. It should be noted that although metal oxide layer 32 is depicted as being disposed along inner surface 33, this is not intended to be limiting as similar metal oxide layers may be formed along the other surfaces of the tubular member 28 as well as along various surfaces of other components of guidewire 10. As can be appreciated in FIG. 2, a portion of the metal oxide layer 32 has been removed from the inner surface 33 of the tubular member 28 near the distal end, for example, where the distal tip 22 is attached, as will be discussed in more detail below.

The presence of the metal oxide may affect the ability of other structures to be bonded to the metal part, for example, through soldering techniques. The presence of the metal oxide can result in solder joints with poor and/or inconsistent characteristics, such as bond strength. The presence of metal oxide layers has been found to be particularly problematic when soldering to certain metals, such as nickel-titanium alloys in the like. For example, if a significant oxide layer is present on the surface of a nickel-titanium alloy member, it can be increasingly difficult to solder another metal member, such as a stainless steel or a nickel-chromium-molybdenum alloy, such as Inconel (Unified Numbering System (UNS) designation of N06625) work piece to the nickel-titanium alloy member and achieve a suitable solder joint. It has been found that the reduction, alteration, and/or removal of such metal oxides from the surface of the metal prior to soldering results in a better solder joint. Some methods of removing oxide from the surface of metal components prior to soldering may include the use of chemical fluxes or the like. However, the use of chemicals is at least sometimes undesirable due, for example, to their harsh nature. In addition, when using fluxes and the like to remove oxide from the surface of a metal, it is often difficult to control the depth and/or size of the treated area where oxide is removed. The variance in size depth and/or size of the treated area can result in inconsistent bond strengths. For example, solder will typically flow and bond better on the surface where oxide has been removed, and tends to stop flowing as freely and bond relatively poorly when it reaches an untreated portion where oxide is more prevalent. If the depth and/or size of the treated areas among different bond areas vary, it is difficult to achieve consistent solder bonds. As such, it may be desirable to provide alternative structures and/or methods for treating and/or removing at least portions of oxide layers from the inner surface of a metallic tubular member such that soldering techniques can be utilized to attach other components of a device to the inner surface of the tubular member 28.

In that regard, the use of mechanical honing and/or scoring means and/or methods to score the oxide on the inner surface of the tubular member 28 can be used in at least some embodiments. Some of these mechanical honing and/or scoring methods and/or means are discussed below. This differs from other methodologies that primarily utilize harsh chemicals to remove the metal oxide layer that can form on the inside surface of a metal tubular member. Because scoring can be accomplished mechanically, the use of these chemicals can be reduced if not eliminated. Additionally, it has been found that in at least some cases, the use of mechanical scoring can often provide good control for the depth and/or size of the scored area. Such control can provide for better and/or more consistent bond areas and/or bond strengths.

For example, in at least some embodiments, a portion of the inner surface 33 of the tubular member 28 can be mechanically scored, using mechanical scoring techniques, to alter and/or remove at least a portion of metal oxide layer 32 from inner surface 33. As used herein, mechanical honing and/or scoring can include the mechanical modification of an oxide on a surface, and in at least some embodiments, involves the mechanical removal of at least a portion of the oxide from the surface, for example, to expose non-oxidized metal at the surface. A surface that is mechanically scored includes the mechanical modifications of the oxide on a surface, and in at least some embodiments, has oxide mechanically removed there from. Such mechanical scoring can result in defining a bonding zone on the surface that has oxide that is mechanically modified and/or removed there from, and as such, can provide for an enhanced surface for attachment of solder material. In at least some cases, a mechanically scored surface, or bonding zone, can include a higher percentage of non-oxidized metal at the surface thereof relative to portions that have not been mechanically scored. In some embodiments, the mechanical scoring can entail the removal of substantially all of the pre-existing metal oxide from at least a portion of the surface, leaving a relatively high percentage of non-oxidized metal. In addition, scoring may also be understood to alter the surface texture of a metal oxide layer. For example, the use of the terms "hone" or "score" in relation to metal oxide layer 32 can be understood to mean that metal oxide layer 32 is mechanically altered, scratched, scraped, and/or removed, etc.

Mechanically scoring can remove and/or alter all or portions of the "thickness" (i.e., all or portions of metal oxide layer 32 in the radial direction or the direction that is perpendicular to the longitudinal axis of tubular member 28) of metal oxide layer 32. In addition, scoring can remove all or portion of the "length" of metal oxide layer 32 (i.e., all or portions of metal oxide layer 32 in the direction that is parallel to the longitudinal axis of tubular member 28).

In that regard, one of the steps for manufacturing guidewire 10 might include mechanically scoring the inner surface 33 of the tubular member 28 to remove and/or alter at least a portion of the oxide 32 to create a bonding zone, and thereafter attaching other components of the guidewire to the bonding zone using soldering techniques.

Figure 3:
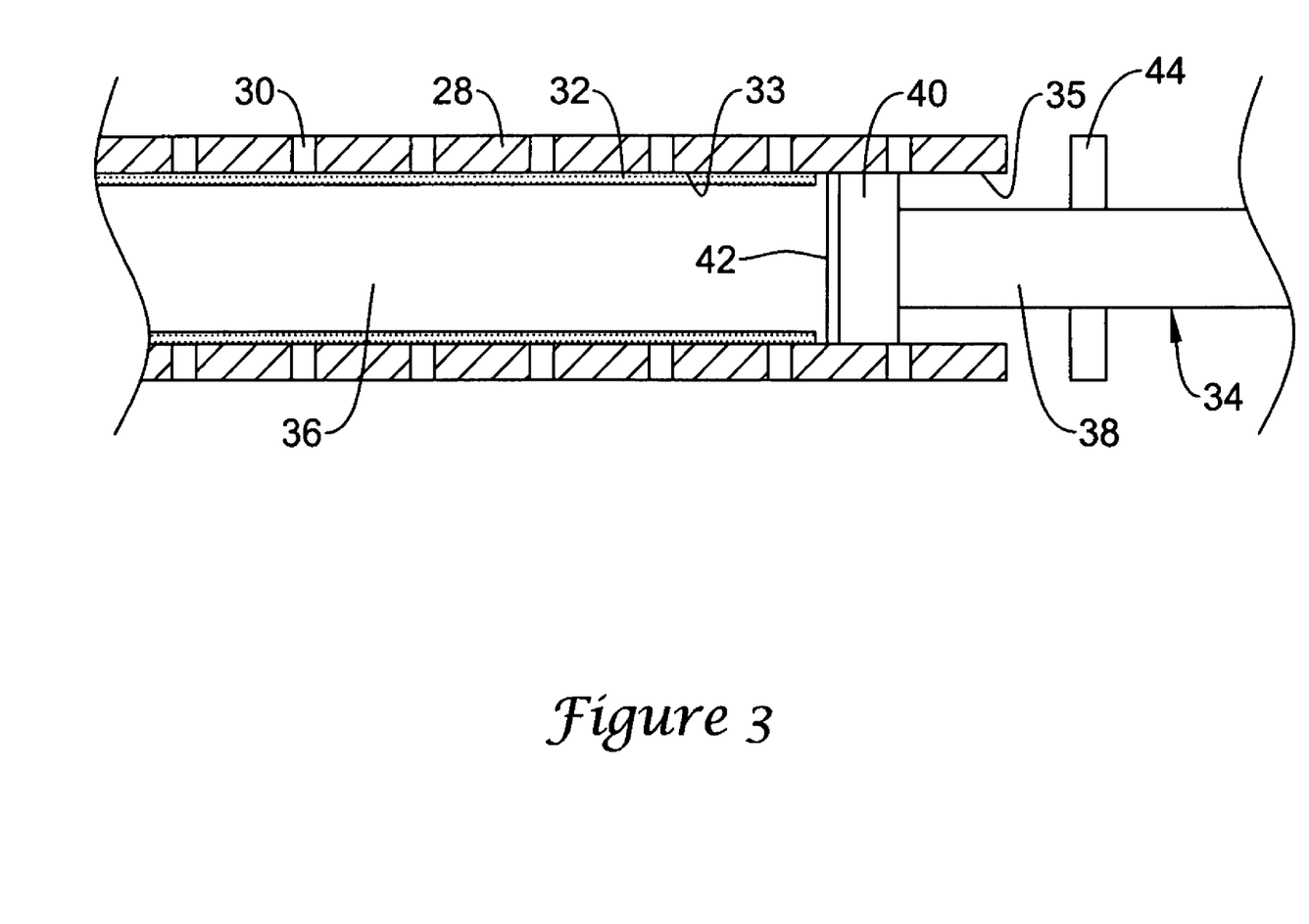
FIG. 3 is a partial cross-sectional side view of an example tubular member where a portion of a scoreable layer is being scored and/or removed from the inner surface of the tubular member.

For example, refer now to FIGS. 3-7 for a discussion of one example embodiment. In FIG. 3, the metallic tubular member 28 is provided, including, for example an oxide 32 formed on inner surface 33. As can be seen, a tool for scoring the inner surface is provided, such as a scoring member and/or tool 34, or the like, that can be used to mechanically score the inner surface of the tubular member 28. The scoring member may be any of a wide variety of tools and/or members that can be configured and/or adapted to mechanically score the inner surface of the tubular member 28. Some examples of scoring tools and/or members can include a mill, such as an end mill, a drill, a router, a reamer, a cutting or abrasive wire or other structure, such as a diamond wire or the like, and/or the associated bits and/or cutting components for use with such tools. The scoring member 34 can be operated and/or inserted within the lumen 36 of tubular member 28 so as to score the metal oxide layer 32 and create a bonding zone 35 along inner surface 33. In at least some embodiments, at least a portion of the oxide layer 32 is removed from inner surface 33 within the bonding zone. Scoring member 34 may include a base region 38 and a scoring or cutting region 40. Scoring region 40 may include a blade or cutting member 42 that is configured to score, cut, ablate, and/or remove at least a portion of metal oxide layer 32. In some embodiments, cutting member 42 may include a rotary blade. These embodiments may be associated with the removal of a portion of metal oxide layer 32. In other embodiment, cutting member 40 may include an abrasive or scoring blade that ablates the metal oxide layer 32. Of course, numerous other versions and/or variations of scoring members 34 are contemplated for scoring and/or removing a portion of metal oxide layer 32.

Scoring member 34 may also be used to control the size of the area scored, for example to control the size of the bonding zone. For example, the careful application of the scoring member 34 to score only a desired length and/or area of the inner surface can define consistently sized and/or shaped bonding zones among a number of tubular members 28. In some embodiments, the scoring member 34 may include a stop member 44, or the like, that can be disposed on the scoring member 34, for example along body region 38, to control the length along which metal oxide layer 32 is scored and/or removed and, consequently, the length of bonding zone 35. This control of the bonding zone size can also help to control the length that solder travels along inner surface 33 of tubular member 28, because solder tends to not flow easily along metal oxide layer 32. As such, more consistent solder bonds may be achieved. The use of such a stop member 44, which is optional, may include positioning stop member 44 at the desired position along body region 38 (e.g., about 1-120 millimeters from blade 42) so that when scoring member 34 is inserted into lumen 36, stop member 44 will catch on the end of tubular member 28 and prevent scoring member 34 from traveling deeper within tubular member 28. Alternatively, stop member 44 can be left off of honing member 34 so that the entire length of metal oxide layer 32 can be removed and/or scored.

Additionally, the scoring member 34 may also be adapted and/or configured to remove a desired thickness of material from the inner surface 33. For example, the scoring member 34 may have an effective cutting diameter that is slightly larger than that of the inner diameter of the tubular member 28, and the difference in size can be adapted to remove a desired amount of material. In some embodiments, the effective cutting diameter of the scoring member 34 can be in the range of 0.00005 to about 0.0005 inches larger than the inner diameter of the tubular member 28 for effective scoring of the inner surface, but without the removal of to much material from the tubular member. However, these sizes are given by way of example only, and it is contemplated that others may be used.

Regardless of whether metal oxide layer 32 is removed or altered, the mechanical alteration of metal oxide layer 32 creates the bonding zone that allows an additional structural element to be more effectively soldered to tubular member 28. For example, solder may be able to flow into and bond to inner surface 33 of tubular member 28 adjacent bonding zone 35. For example, a distal tip 22, or other structure, can be soldered to the bonding zone 35, as will be discussed further below.

Figure 4:
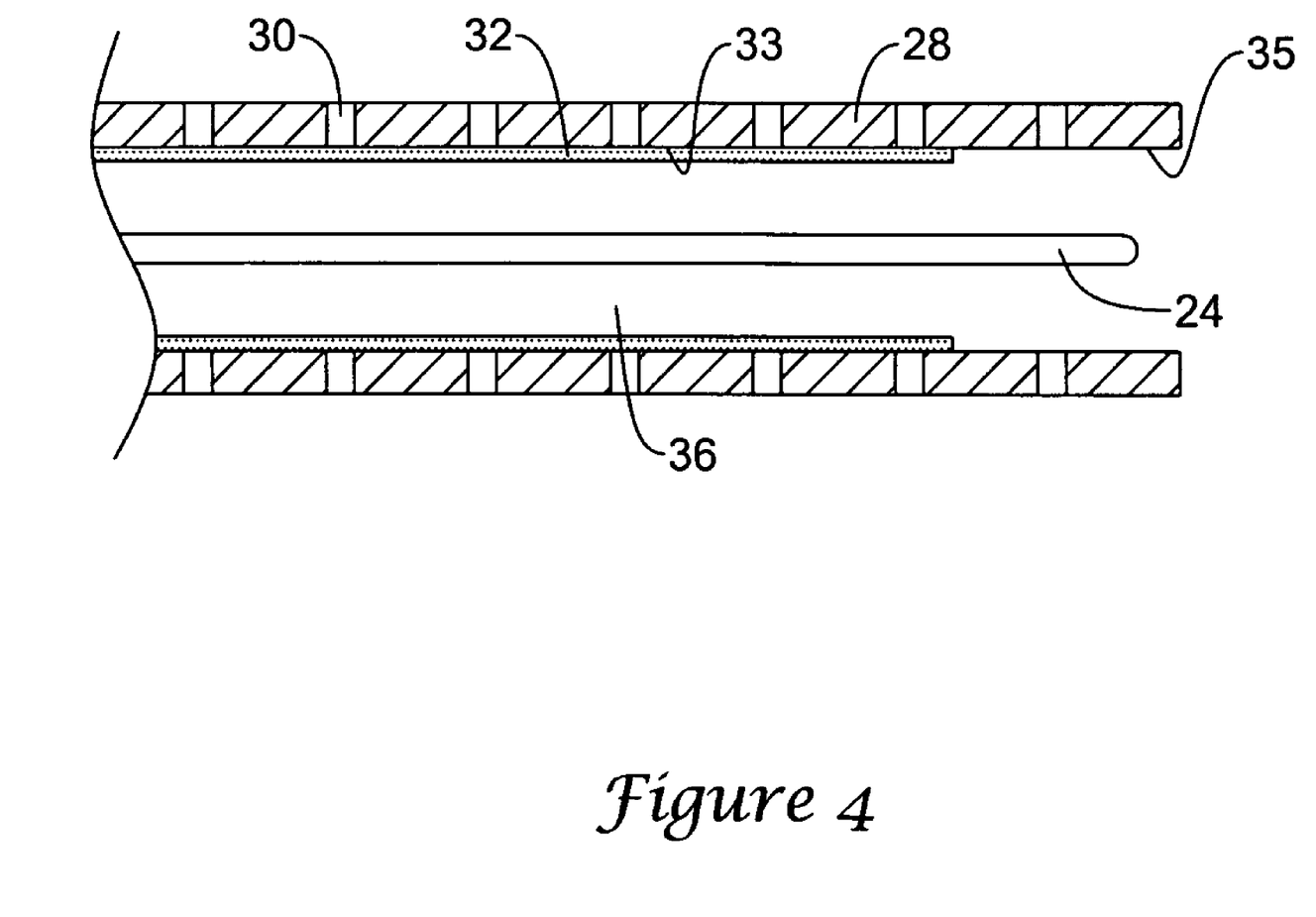
FIG. 4 is a partial cross-sectional side view of the tubular member depicted in FIG. 3 with a core wire disposed therein.
Figure 5:
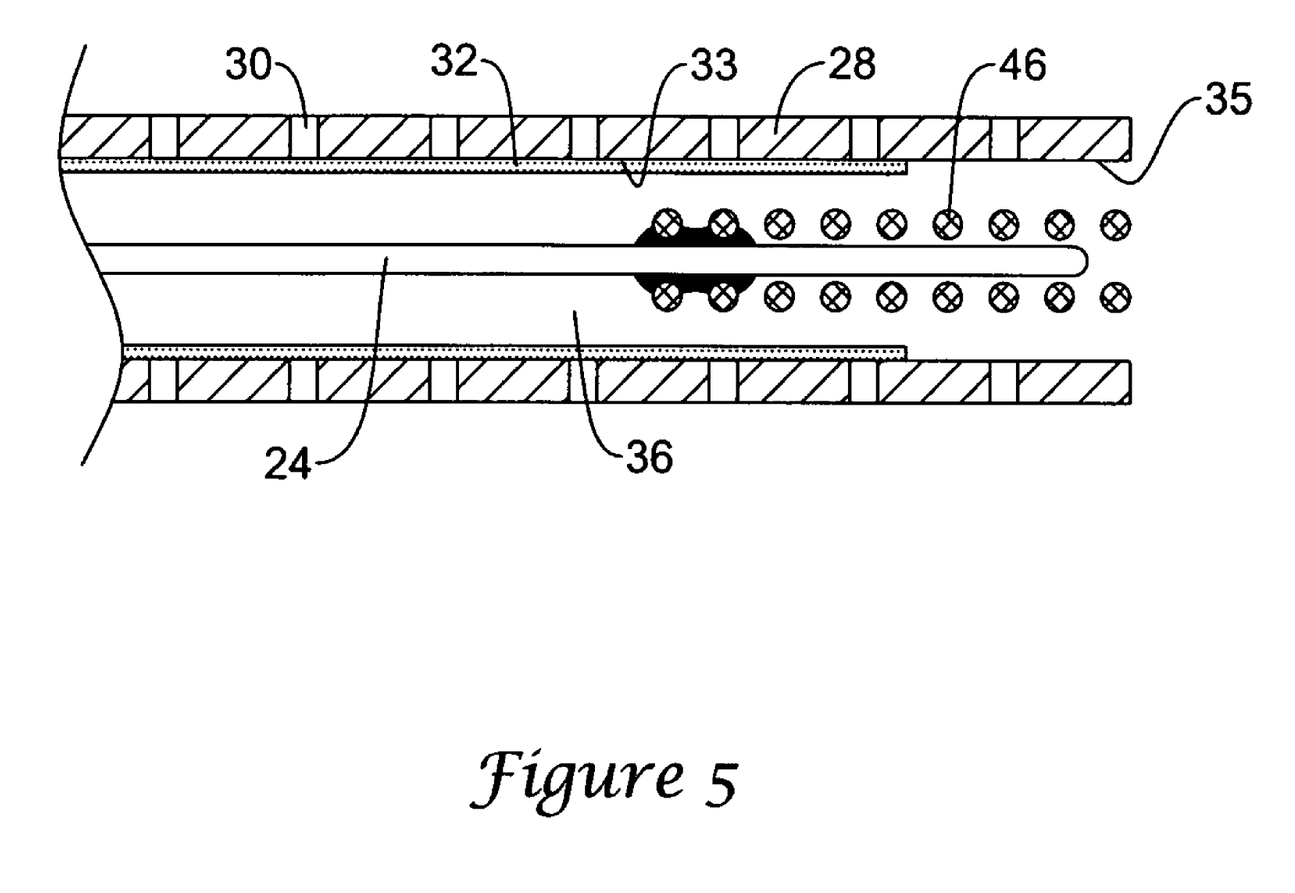
FIG. 5 is a partial cross-sectional side view of the tubular member and core wire depicted in FIG. 4 with a coil disposed in the tubular member.

With metal oxide layer 32 scored and/or removed to the desired extent to create the bonding zone 35, further manufacturing steps may be taken to complete the assembly of guidewire 10. For example, core wire 24 may be disposed within tubular member 28 as depicted in FIG. 4. Moreover, other structures, such as a coil 46 may be disposed within lumen 36 adjacent core wire 24 as shown in FIG. 5. A number of additional steps may also be performed, depending on the design of guidewire 10, in order to add any one of a number of features or characteristics to guidewire 10.

Figure 6:
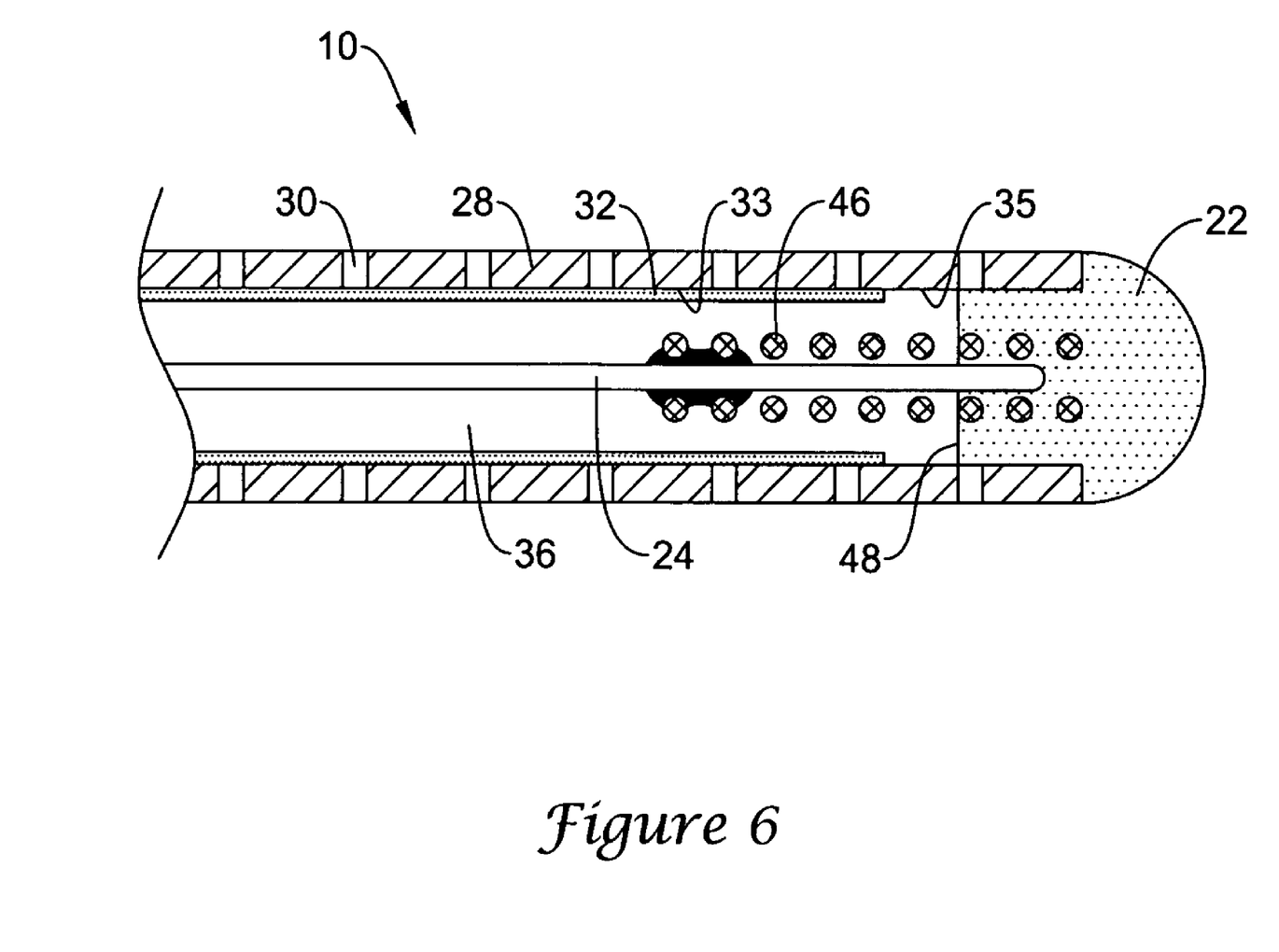
FIG. 6 is a partial cross-sectional side view of the tubular member, core wire, and coil depicted in FIG. 5 with a solder bead disposed adjacent the tubular member and forming a distal tip.
Figure 7:
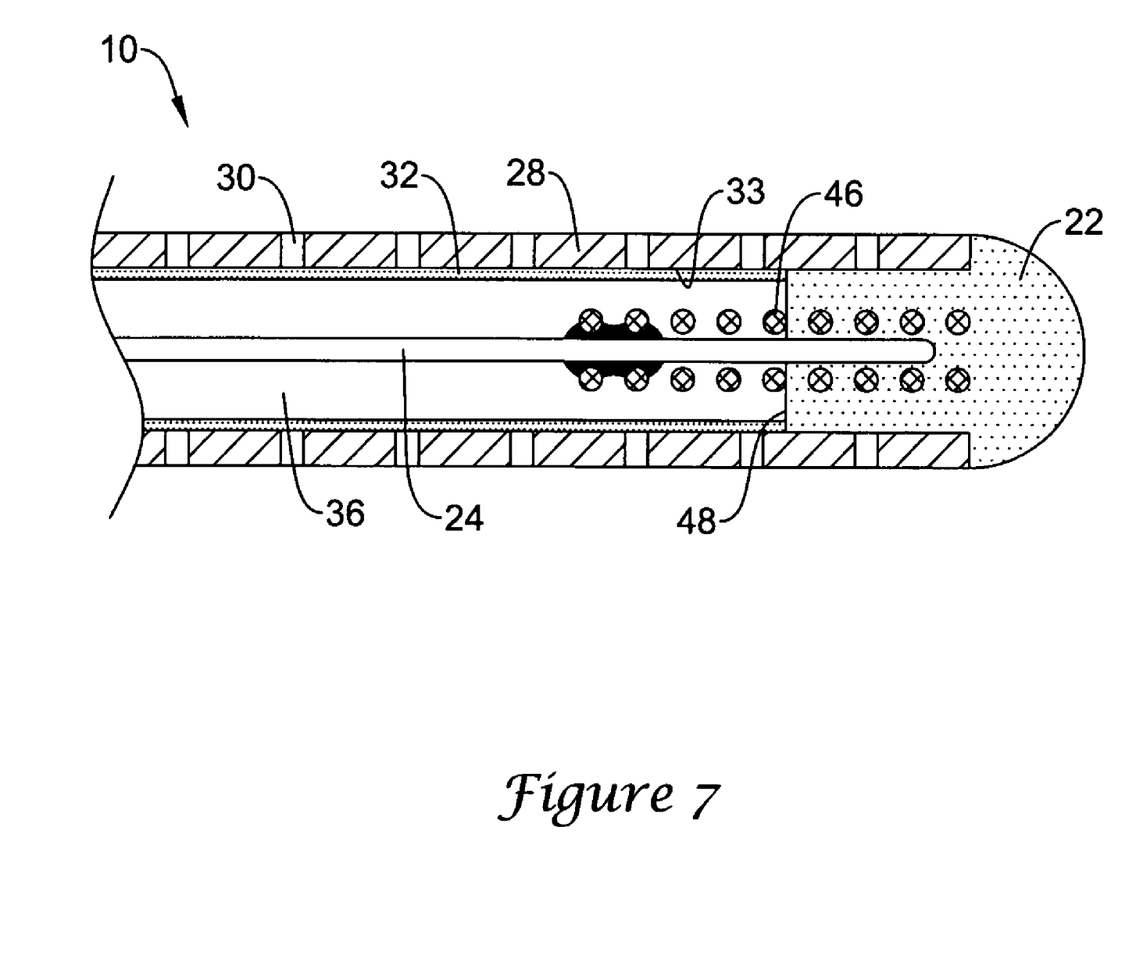
FIG. 7 is a partial cross-sectional side view of the tubular member, core wire, coil, and solder bead depicted in FIG. 6 where a portion of the solder has flowed along the inner surface of the tubular member where the portion of the scoreable layer has been removed.

FIG. 6 shows the beginning of the step of soldering an additional structural element to bonding zone 35. For example, distal tip 22 (or a solder ball or solder bead that defines distal tip 22) may be disposed on or adjacent the end of tubular member 28 and heated such that it flows. Here it can be seen that a leading edge 48 of solder (i.e., the material making up distal tip 22) has partially migrated along the inner surface 33 of tubular member 28 where metal oxide layer 32 is scored and/or removed (i.e., along bonding zone 35). Eventually, leading edge 48 may abut and/or overlap with metal oxide layer 32 as shown in FIG. 7. The distal end of the tip may be provided with a generally rounded and/or atraumatic distal surface. The distal tip 22 may secure together tubular member 28, core wire 24, and coil 46. It should be noted that the steps of adding and/or attaching a solder ball, a solder bead, or a distal tip to the end of guidewire 10 (e.g., to the end of tubular member 28) as well as the step of soldering a distal tip (or any other additional structural element that might, for example, define distal tip 22) are understood to be generally similar steps, and phrases describing these steps or the structures associated with these steps can be used interchangeably.

It should be noted that although the above discussion is focused on scoring tubular member 28 in order to attach distal tip 22 to tubular member 28, this is not intended to be limiting. Essentially any portion of metal oxide layer 32 (or all of it) can be removed to facilitate the bonding of essentially any suitable structure (e.g., core wire 24, coil 46, etc.) to tubular member 28. For example, a proximal portion of metal oxide layer 32 can be removed from tubular member 28 to facilitate bonding (e.g., via soldering) between tubular member 28 and core wire 24. Additionally, as can be appreciated, by the use of a solder tip, the distal tip of the core wire, and the distal tip of the coil may also be considered to be soldered to the inner surface of the tubular member. Similarly, the removal and/or scoring of a metal oxide layer can also be carried out on core wire 24, coil 46, or any other suitable structure to similarly facilitate bonding.

As suggested above, distal tip 22 may include solder attached to the inner surface of the tubular member at the bond zone, and/or a solder material is used to attach a structural component to the bond zone. Any suitable solder material may be used given the particular materials being joined. Some examples of suitable solders may include a tin/silver solder, a tin/bismuth solder, a tin/gold solder, or the like, or any other suitable solder. In addition, it may be desirable to add an effective quantity of flux (e.g., a phosphoric acid based flux or any other suitable flux) to the solder and/or to the materials being joined so as to enhance the flowability of the solder within tubular member 28. However, as discussed above, the amount and/or necessity of such a flux may be reduced due, for example, to the mechanical removal of oxide, and in some embodiments, the use of such a flux may not be necessary. For example, in some embodiments, a small amount of flux may be placed on the area to be soldered, such as up to a few drops of phosphoric acid based flux, such as Indalloy Flux #2. The solder may be disposed in place using any suitable soldering technique, and up to a few more drops of flux may be added, and heat, for example, from a soldering iron or the like, can be applied to flow the solder into place. However, those of skill in the art and others will recognize that there are a broad variety of soldering techniques and/or structures that may be utilized, and that this is given by way of example only.

The materials that can be used for the various components of guidewire 10 may include those commonly associated with medical devices. For example, core wire 24 and/or tubular member 28, and various other components of guidewire 10 may be made from any suitable material such as a metal, metal alloy, a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As alluded to above, within the family of commercially available nickel-titanium or nitinol alloys, is a category designated "linear elastic" which, although is similar in chemistry to conventional shape memory and superelastic varieties, exhibits distinct and useful mechanical properties. By applications of cold work, directional stress, and heat treatment, the material is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there are no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of guidewire 10 such as core wire 24 and/or tubular member 28 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. In some other embodiments, a superelastic alloy, for example a superelastic nitinol can be used to achieve desired properties.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

As suggested above, core wire 24 may include one or more distal tapers or regions 26 that otherwise decrease in outer diameter. Forming tapered regions 26 may include any one of a number of different techniques. For example, tapered regions 26 may be formed by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire 24 during the grinding process. In some embodiments, core wire 26 is centerless ground using a Royal Master HI-AC centerless grinder.

In some embodiments, a degree of MRI compatibility is imparted into device 10. For example, to enhance compatibility with Magnetic Resonance Imaging (MRI) machines, it may be desirable to make core wire 24 and/or tubular member 28, or other portions of guidewire 10, in a manner that would impart a degree of MRI compatibility. For example, core wire 24 and/or tubular member 28, or portions thereof, may be made of a material that does not substantially distort the image and create substantial artifacts (artifacts are gaps in the image). Certain ferromagnetic materials, for example, may not be suitable because they may create artifacts in an MRI image. Core wire 24 and/or tubular member 28, or portions thereof, may also be made from a material that the MRI machine can image. Some materials that exhibit these characteristics include, for example, tungsten, Elgiloy, MP35N, nitinol, and the like, and others.

In at least some embodiments, tubular member 28 includes a plurality of slots 30 formed therein as indicated above. Slots 30 may be micromachined or otherwise created in tubular member 28, and may be configured to make tubular member 28 more flexible in bending. It is worth noting that, to the extent applicable, the different configurations for slots 30 and/or methods for forming slots 30 can include, for example, any of those disclosed in U.S. Pat. Publication No. US 2003/0069522, U.S. Pat. Publication No. 2004/0181174 A2, and/or U.S. Pat. No. 6,766,720, the entire disclosures of which are herein incorporated by reference. These and other cutting methods may also include saw cutting (e.g., diamond grit embedded semiconductor dicing blade), etching (for example using the etching process described in U.S. Pat. No. 5,106,455, the entire disclosure of which is herein incorporated by reference), laser cutting, electron discharge machining, or the like. It should be noted that the methods for manufacturing guidewire 10 may include forming slots 30 in tubular member 28 using any of these or other manufacturing steps.

Various embodiments of arrangements and configurations of slots 30 are contemplated. Slots 30 may be generally arranged to be perpendicular to the longitudinal axis of tubular member 28. This arrangement can, alternatively, be described as having slots 30 lying within a plane that is normal to the longitudinal axis of tubular member 28. In other embodiments, slots 30 may be formed at an angle relative to a plane that is normal to the longitudinal axis. In some embodiments, slots 30 may be formed part way through tubular member 28, while in other embodiments, slots 30 may extend all the way through tubular member 28. Any one or more of the individual slots 30 may extend only partially around the longitudinal axis of tubular member 28. In yet other embodiments, slots 30 may extend in a helical arrangement about the longitudinal axis of tubular member 28. Slots 30 may be formed in groups of two, three, or more slots 30, which may be located at substantially the same location along the axis of tubular member 28, and may be substantially perpendicular to the longitudinal axis.

Coil 46 may also be disposed adjacent tubular member 28 and/or distal tip 22. In at least some embodiments, coil 46 includes a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, iridium, bismuth, molybdenum, palladium, tantalum, tungsten or tungsten alloy, plastic material loaded with a radiopaque filler, and the like. Other components of guidewire 10 may similarly include a radiopaque material.

Although set forth with specific reference to guidewires in some of the example embodiments shown in the Figures and discussed above, the invention may relate to virtually any medical device including an elongate metallic tubular member and additional structures soldered to the inner surface of the tubular member. For example, the invention may be applied to medical devices such as a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a guidewire, in other applications, sizes in terms of diameter, width, and length may vary widely, depending upon the desired properties of a particular device.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention.

What is claimed is:

1. A method for manufacturing an intravascular medical device, the method comprising:
   providing an elongate metallic tubular member defining an inner lumen and having an inner surface, the inner surface including a metal oxide formed thereon;
   providing an elongate core wire having a proximal end, a distal end, and at least one tapered region adjacent the distal end;

inserting a scoring tool into the lumen of the tubular member;
mechanically scoring at least a portion of the inner surface to remove at least some of the metal oxide with the scoring tool to create a bonding zone along the inner surface;
disposing the core wire in the lumen of the tubular member;
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;
attaching a proximal end of the coil member to the core wire; and
soldering a distal tip to the bonding zone;
wherein the distal end of the coil member extends distally into the distal tip; and
wherein the scoring tool includes a rotary blade.

2. The method of claim 1, wherein the distal tip includes solder.

3. The method of claim 1, wherein the tubular member includes a nickel-titanium alloy.

4. The method of claim 1, wherein the tubular member includes a plurality of slots formed therein.

5. The method of claim 1, wherein the scoring tool includes a mill.

6. The method of claim 1, wherein the scoring tool includes a drill bit.

7. The method of claim 1, wherein the scoring tool includes a router bit.

8. The method of claim 1, wherein the scoring tool includes a reamer bit.

9. The method of claim 1, wherein the scoring tool includes a diamond wire.

10. A medical device formed by the method of claim 1.

11. A method for manufacturing an intravascular medical device, the method comprising:
providing an elongate metallic tubular member defining an inner lumen and having an inner surface, the inner surface including a metal oxide formed thereon;
providing an elongate core wire having a proximal end, a distal end, and at least one tapered region adjacent the distal end;
inserting a scoring tool into the lumen of the tubular member;
mechanically scoring at least a portion of the inner surface to remove at least some of the metal oxide with the scoring tool to create a bonding zone along the inner surface;
disposing the core wire in the lumen of the tubular member;
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;
attaching a proximal end of the coil member to the core wire; and
soldering a distal tip to the bonding zone;
wherein the distal end of the coil member extends distally into the distal tip;
wherein the scoring tool includes a cutting member; and
wherein the metal oxide has a length and a thickness and wherein mechanically scoring at least a portion of the inner surface to remove at least some of the metal oxide to create a bonding zone along the inner surface includes removing only a portion of the thickness of the metal oxide.

12. The method of claim 11, wherein soldering a distal tip to the bonding zone includes disposing solder along the inner surface of the tubular member where the portion of the thickness of the metal oxide is removed.

13. The method of claim 11, wherein mechanically scoring at least a portion of the inner surface to remove at least some of the metal oxide to create a bonding zone along the inner surface includes removing only a portion of the thickness of the metal oxide along only a portion of the length of the metal oxide.

14. The method of claim 13, wherein soldering a distal tip to the bonding zone includes disposing solder along the inner surface of the tubular member where the portion of the thickness of the metal oxide is removed.

15. The method of claim 11, wherein mechanically scoring at least a portion of the inner surface to remove at least some of the metal oxide to create a bonding zone along the inner surface includes removing only a portion of the thickness of the metal oxide along substantially all of the length of the metal oxide.

16. The method of claim 15, wherein soldering a distal tip to the bonding zone includes disposing solder along the inner surface of the tubular member where the portion of the thickness of the metal oxide is removed.

17. A method for manufacturing an intravascular medical device, the method comprising:
providing an elongate metallic tubular member defining an inner lumen and having an inner surface, the inner surface including a metal oxide formed thereon;
providing an elongate core wire having a proximal end, a distal end, and at least one tapered region adjacent the distal end;
inserting a scoring tool into the lumen of the tubular member;
mechanically scoring at least a portion of the inner surface to remove at least some of the metal oxide with the scoring tool to create a bonding zone along the inner surface;
disposing the core wire in the lumen of the tubular member;
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;
attaching a proximal end of the coil member to the core wire; and
soldering a distal tip to the bonding zone;
wherein the distal end of the coil member extends distally into the distal tip;
wherein the scoring tool includes a cutting member; and
wherein the metal oxide has a length and a thickness and wherein mechanically scoring at least a portion of the inner surface to remove at least some of the metal oxide to create a bonding zone along the inner surface includes removing substantially all of the thickness of the metal oxide along only a portion of the length of the metal oxide.

18. The method of claim 17, wherein soldering a distal tip to the bonding zone includes disposing solder along the inner surface of the tubular member where the portion of the thickness of the metal oxide is removed.

19. A method for manufacturing an intravascular medical device, the method comprising:
providing an elongate metallic tubular member defining an inner lumen and having an inner surface, the inner surface including a metal oxide formed thereon;
providing an elongate core wire having a proximal end, a distal end, and at least one tapered region adjacent the distal end;
inserting a scoring tool into the lumen of the tubular member;
mechanically scoring at least a portion of the inner surface to remove at least some of the metal oxide with the scoring tool to create a bonding zone along the inner surface;
disposing the core wire in the lumen of the tubular member;
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;
attaching a proximal end of the coil member to the core wire; and
soldering a distal tip to the bonding zone;
wherein the distal end of the coil member extends distally into the distal tip;
wherein the scoring tool includes a cutting member; and
wherein the metal oxide has a length and a thickness and wherein mechanically scoring at least a portion of the inner surface to remove at least some of the metal oxide to create a bonding zone along the inner surface includes removing substantially all of the thickness of the metal oxide along substantially all of the length of the metal oxide.

20. The method of claim 19, wherein soldering a distal tip to the bonding zone includes disposing solder along the length of the metal oxide where the thickness of the metal oxide is removed.

21. A method for manufacturing an intravascular medical device, the method comprising:
providing an elongate metallic tubular member defining an inner lumen and having an inner surface, the inner surface including a metal oxide formed thereon;
providing an elongate core wire having a proximal end, a distal end, and at least one tapered region adjacent the distal end;
inserting a scoring tool into the lumen of the tubular member;
mechanically scoring at least a portion of the inner surface to remove at least some of the metal oxide with the scoring tool to create a bonding zone along the inner surface;
disposing the core wire in the lumen of the tubular member;
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;
attaching a proximal end of the coil member to the core wire; and
soldering a distal tip to the bonding zone;
wherein the distal end of the coil member extends distally into the distal tip;
wherein the scoring tool includes a cutting member; and
wherein the metal oxide has a surface texture and wherein mechanically scoring at least a portion of the inner surface to remove at least some of the metal oxide to create a bonding zone along the inner surface includes altering the surface texture.

22. A method for manufacturing a guidewire, comprising the steps of:
providing an elongate nickel titanium alloy tubular member defining an inner lumen and having an inner surface, the inner surface including a metal oxide formed thereon, the tubular member including a proximal end and a distal end, and a plurality of slots formed therein;
mechanically scoring at least a portion of the inner surface adjacent the distal end to remove at least some of the metal oxide with a scoring tool from the inner surface to create a bonding zone;
disposing at least a portion of an elongate core wire within the lumen such that a distal end of the core wire is disposed adjacent the bonding zone;
disposing a coil member adjacent the tubular member; and
soldering at least a portion of the distal end of the core wire to at least a portion of the bonding zone, wherein soldering at least a portion of the distal end of the core wire to at least a portion of the bonding zone secures the coil to the tubular member and to the core wire;
wherein the scoring tool including a rotary blade.

23. The method of claim 22, wherein the metal oxide has a length and a thickness and wherein mechanically scoring at least a portion of the inner surface adjacent the distal end to remove at least some of the metal oxide from the inner surface to create a bonding zone includes removing only a portion of the thickness of the metal oxide.

24. The method of claim 22, wherein removing only a portion of the thickness of the metal oxide includes removing only a portion of the thickness of the metal oxide along only a portion of the length of the metal oxide.

25. The method of claim 22, wherein removing only a portion of the thickness of the metal oxide includes mechanically scoring the inner surface of the tubular member with a mill, a drill bit, a router bit, a reamer bit, or a diamond wire.

26. The method of claim 22, wherein the coil includes a radiopaque material.

27. The method of claim 22, further comprising adding an effective amount of flux during the soldering step.

28. The method of claim 22, wherein soldering at least a portion of the distal end of the core wire to at least a portion of the bonding zone includes defining a distal tip at the distal end of the tubular member.

29. A medical device formed by the method of claim 22.

30. A method for manufacturing a guidewire, comprising the steps of:
providing a nickel-titanium alloy tubular member having a distal end and defining a lumen therein;
wherein the tubular member has an inner surface having a metal oxide formed thereon;
forming a plurality of slots in the tubular member;
inserting a scoring tool into the lumen;
mechanically removing at least a portion of the metal oxide with the scoring tool to create a bonding zone;
disposing a core wire in the tubular member; and
attaching the core wire to the tubular member at one or more attachment points adjacent to a proximal end of the tubular member;
disposing a coil member over the distal end of the core wire and within the lumen of the tubular member such that a distal end of the coil member is disposed adjacent the bonding zone;

attaching a proximal end of the coil member to the core wire; and disposing a bead of solder at the distal end of the tubular member to form a distal tip and allowing a portion of the solder to flow within the tubular member along the inner surface of the tubular member where the metal oxide is removed, wherein the distal end of the coil member extends distally into the distal tip;

wherein the scoring tool is selected from the group consisting of a mill, a drill bit, a router bit, a reamer bit, and a diamond wire.

31. A medical device formed by the method of claim 30.

32. A guidewire comprising:

an elongate tubular member including a proximal end and a distal end, and a plurality of slots formed therein, the tubular member defining an inner lumen and having an inner surface, a portion of the inner surface being mechanically scored with a scoring tool including a rotary blade such that it defines a bonding zone adjacent the distal end of the tubular member having a reduced amount of metal oxide; and an elongate core wire having a proximal end, a distal end, and at least one tapered region adjacent the distal end, at least a portion of the distal end of the core wire disposed within the lumen of the tubular member;

a coil member disposed over the distal end of the core wire and within the lumen of the tubular member such that a distal end of the coil member is disposed adjacent the bonding zone;

a distal tip soldered to the inner surface at the bonding zone; and wherein the tubular member comprises a nickel-titanium alloy.

33. The elongated medical device of claim 32, wherein the distal end of the core wire is disposed adjacent the bonding zone and soldered to the bonding zone.

34. The elongated medical device of claim 33, wherein the distal tip is a solder tip, and the core wire is soldered to the bonding zone with solder material form the distal tip.

* * * * *